United States Patent [19]

Wolfson

[11] Patent Number: 5,281,228
[45] Date of Patent: Jan. 25, 1994

[54] UMBILICAL CLAMP IDENTIFICATION DEVICE FOR INFANTS

[76] Inventor: Fred Wolfson, 1800 N. Highland #120, Los Angeles, Calif. 90028

[21] Appl. No.: 979,843

[22] Filed: Nov. 23, 1992

[51] Int. Cl.⁵ .............................. A61B 17/42
[52] U.S. Cl. ........................ 606/120; 606/157; 40/300; 40/316
[58] Field of Search ........... 606/120, 151, 157, 158; 40/300, 301, 302, 642, 316, 658, 666, 906, 633, 651, 652, 653

[56] References Cited

U.S. PATENT DOCUMENTS

| | | | |
|---|---|---|---|
| 204,736 | 6/1878 | Housum et al. | 40/300 |
| 1,320,426 | 11/1919 | Spurling | 40/302 |
| 1,470,280 | 10/1923 | McCulloch | 40/658 |
| 2,434,831 | 1/1948 | Brandenburg | 606/120 |
| 3,197,899 | 8/1965 | Twentier | 40/633 |
| 4,212,303 | 7/1980 | Nolan | 606/120 |

*Primary Examiner*—Tamara L. Graysay
*Attorney, Agent, or Firm*—Graham & James

[57] ABSTRACT

An umbilical clamp which includes an identification label affixed to or placed within the clamp in a manner such that once the clamp is placed about the umbilical cord of the infant, the identification label cannot be removed.

5 Claims, 1 Drawing Sheet

UMBILICAL CLAMP IDENTIFICATION DEVICE FOR INFANTS

BACKGROUND OF THE INVENTION

The present invention is directed to an apparatus for identification and control of access to a newborn infant. More specifically, the present invention is directed to a clamp including an identification label for placement on the umbilical cord of the newborn infant.

Presently, newborn infants are identified by placement of a wristband and/or an ankleband about the respective limb of the infant. By necessity, the wristband or ankleband must be placed so as to be loose, to prevent restricting of the circulation. Because of the placement of the wristband and/or ankleband, in combination with the normal movement including kicking and hand waving which a newborn infant normally practices, it is not uncommon for the wristband and/or the ankleband to become dislodged, whereby the infant no longer has an identification attached to their body.

The cost associated with misidentification of newborn infants, with respect to both insurance to the attending hospital as well as the emotional impact on the parents, is difficult to measure. However, in a hospital which routinely handles multiple newborns simultaneously, it is a constant fear that two infants will be switched, or alternatively that an infant will be kidnapped. Thus, it is very important for both the hospital and the parents that the newborn infant be identified in a manner which is secure and which prevents removal by non-parents or non-hospital staff.

Accordingly, it would be beneficial to have an identification system which fixes securely to the newborn infant and which cannot easily be removed or altered.

SUMMARY OF THE INVENTION

The present invention is directed to an umbilical clamp which includes an identification label placed within the clamp in a manner such that once the clamp is placed about the umbilical cord of the infant, the identification label cannot be removed. In addition, since the umbilical clamp is necessary for approximately the first 10 to 14 days, i.e. until the umbilical cord naturally detaches, the opportunity for accidental removal of the identification mechanism is eliminated. If the umbilical clamp were to be taken off of the infant, the infant would immediately start hemorrhaging through the umbilical cord.

DETAILED DESCRIPTION OF THE PREFERRED EMBODIMENT

Figure 1:
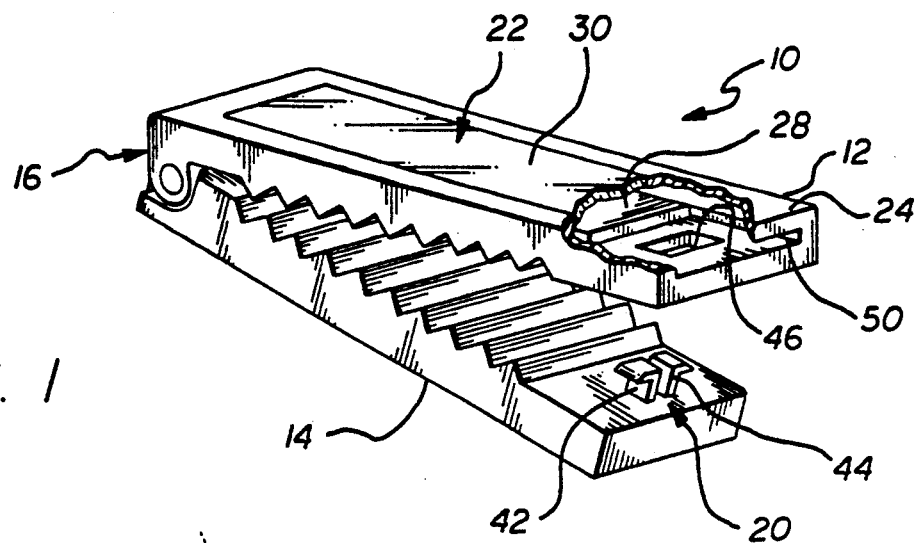
FIG. 1 is a schematic, partially cutaway view of an umbilical clamp according to the present invention.
Figure 2:
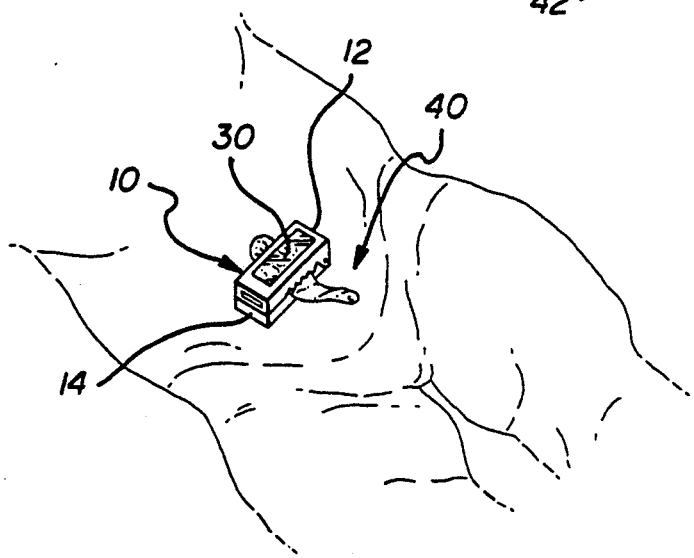
FIG. 2 depicts the umbilical clamp of FIG. 1 placed about the umbilical cord of a newborn infant.

In FIG. 1, an umbilical clamp 10 is illustrated in a schematic view. The umbilical clamp 10 includes a top arm 12 and a bottom arm 14 which are interconnected by a hinge mechanism 16 located at one end of each of the respective arms 12, 14. In addition, the clamp 10 includes a locking mechanism 20 located at the opposite end from the hinge mechanism 16. The top arm 12 includes a means for receiving 22 an identification tag or label 28. The means for receiving 22 may include a slot 24 placed beneath a clear plastic cover 30 into which a label 28 is placed following the marking of the label with the infant's name. The label 28 is inserted into the slot 24, and the umbilical clamp 10 is placed about the umbilical cord of the infant, as shown by 40 in FIG. 2. Upon clamping of the locking mechanism 20, the locking mechanism 20 secures the identification label 28 within the slot 24 thereby preventing its removal and assuring its continued placement within the umbilical clamp 10.

The locking mechanism 20 of the umbilical clamp 10 may simply include a pair of clasps 42, 44 projecting upward from the bottom arm 14, for receivably mating with a slotted opening 46 within the top arm 12. The slotted opening 46 may project all the way through or only partially through the top arm 12, but is preferably configured so that the projecting clasps 42, 44 of the locking mechanism 20 seal an open end 50 of the slot 24, which receives the identification label 28.

By this simple mechanism, the identification of the infant is maintained as long as the umbilical clamp 10 and the umbilical cord remain on the infant. Normally, an infant will not lose their umbilical cord for approximately 10 to 14 days. The duration of time in which the infant must remain in the hospital is normally 2 days or less, and hospitalization for more than a week is infrequent unless the infant has medical complications. Accordingly, for a vast majority of the newborn infants, the umbilical clamp 10 identification device of the present invention provides an easy manner of identifying an infant throughout the duration of their stay in the hospital. By utilization of the umbilical clamp 10, the possibility of accidental dislodging of the identification means for the infant is drastically reduced, thereby potentially reducing hospital insurance costs and the risk of accidental switching of newborn infants between respective parents.

Figure 3:
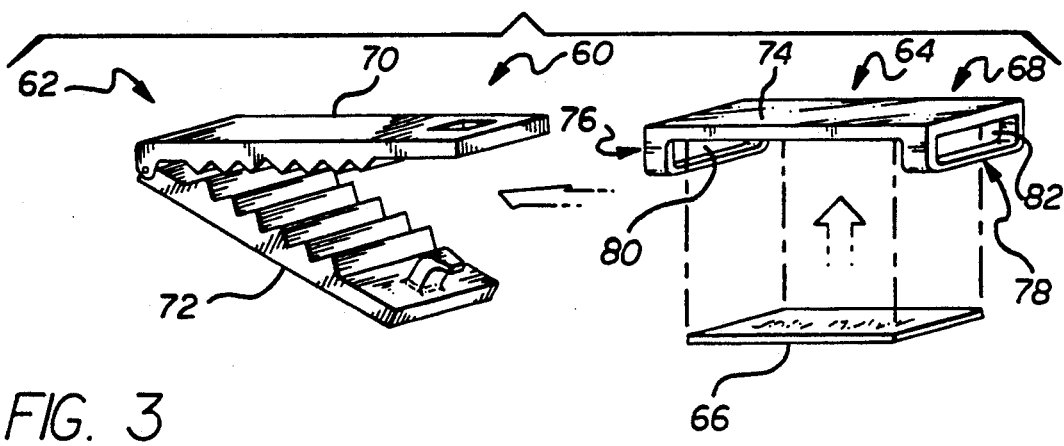
FIG. 3 is an exploded view of an alternative embodiment of the umbilical clamp identification device of the present invention.

FIG. 3 depicts an exploded view of an alternative embodiment of an umbilical clamp identification device 60 also contemplated by the present invention. In FIG. 3, an umbilical clamp 62 as presently utilized in the industry is depicted as receiving an identification means 64. The identification means 64 includes an identification label 66 and a means for securing the identification label 66 to the umbilical clamp 62.

The means for securing may simply be a shield 68 adapted to be affixed to one of the arms 70, 72 of the clamp 62 in a manner such that following closure and locking of the clamp 62, the shield 68 cannot be removed from the clamp 62 without unlocking and opening the clamp 62. Thus, the shield 68 could be a clear plastic element having an elongated portion 74 designed to closely conform to the outer side of the respective arm 70 or 72.

The shield 68 my also include a pair of projections 76, 78 extending from the elongated portion 74, such that the projections 76, 78 extend about the respective arm 70 or 72 of the clamp 62, whereby at least a portion of the projections 76, 78 extends between the upper arm 70 and lower arm 72 of the clamp 62 and is locked therebetween upon closure of the clamp 62. Preferably, the projections 76, 78 form loops 80, 82 which encircle the respective arm 70, 72, and the shield is simply placed over the arm 70 or 72 by inserting the arm through the loops 80, 82.

As may be appreciated, the present invention provides an improvement in the manner in which infants are identified, by providing a simple, inexpensive identification device which can readily replace the present umbilical clamps utilized in the industry. Having provided a description of the preferred embodiment, it is recognized that alternative locking mechanisms or identification labels may be incorporated onto the umbilical clamp in a manner equivalent to that which is now taught by the present invention. Accordingly, while the preferred embodiment has been disclosed, it is anticipated that the scope of the invention will be limited only by the proper interpretation of the appended claims.

What I claim:

1. An umbilical clamp identification device for a newborn infant, comprising:
   an umbilical clamp including an upper arm and a lower arm connected by a hinge, and a locking mechanism for interlocking said upper and lower arms;
   a shield affixed to one of said arms of said clamp, said shield including an elongated portion and at least one projection extending from said elongated portion, said at least one projection extends between said upper arm and said lower arm of said umbilical clamp such that following closure and locking of said clamp, said shield cannot be removed from said clamp without unlocking and opening said clamp; and
   means for identifying the infant, said means for identifying positioned between said shield and said one of said arms of said umbilical clamp.

2. The umbilical clamp of claim 1 wherein said at least one projection comprises:
   a pair of loops, positioned at opposite ends of said elongated portion of said shield, said loops being sized to allow insertion of one of said arms of said umbilical clamp.

3. An umbilical clamp identification device for a newborn infant, comprising:
   an umbilical clamp including an upper arm and a lower arm connected by a hinge; and
   means for identifying the infant, said means affixed to said umbilical clamp, said means for identifying including a slot formed within the upper arm of said umbilical clamp, a window covering said slot, and an identification label placed within said slot.

4. The umbilical clamp of claim 3 further comprising a locking means for locking the upper arm and lower arm of said umbilical clamp in a closed position and for closing an open end of said slot to prevent removal of said identification label.

5. A method of identifying a newborn infant comprising:
   making an identification label including the infant's name;
   securing said identification label to an umbilical clamp by placing said identification label against a transparent shield and securing said transparent shield with said identification label to an arm of said umbilical clamp; and
   securely placing said umbilical clamp about the umbilical cord of said infant and locking said umbilical clamp with a locking mechanism which prevents said transparent shield from being removed without unlocking said locking mechanism.

* * * * *